US008224595B2

(12) United States Patent
Hefner et al.

(10) Patent No.: US 8,224,595 B2
(45) Date of Patent: Jul. 17, 2012

(54) SYSTEM AND METHOD FOR ONLINE MONITORING OF MOLTEN SALT CORROSION

(75) Inventors: Rebecca Evelyn Hefner, Simpsonville, SC (US); Paul Stephen DiMascio, Greer, SC (US)

(73) Assignee: General Electric Company, Schenectady, NY (US)

( * ) Notice: Subject to any disclaimer, the term of this patent is extended or adjusted under 35 U.S.C. 154(b) by 333 days.

(21) Appl. No.: 12/757,636

(22) Filed: Apr. 9, 2010

(65) Prior Publication Data
US 2011/0251721 A1 Oct. 13, 2011

(51) Int. Cl.
*G01N 27/04* (2006.01)
(52) U.S. Cl. .......... 702/57; 324/700; 204/404; 204/412; 204/422; 204/408; 204/196.02; 204/419; 205/775.5; 205/793; 205/794.5; 205/786; 700/275; 700/287; 700/288
(58) Field of Classification Search .............. 702/57; 324/700, 444, 437, 451, 696, 713; 204/400, 204/404, 410, 412, 422, 408, 419, 196.02, 204/196.01; 205/775.5, 790, 793, 794.5, 205/783.5, 786; 700/275, 287, 288
See application file for complete search history.

(56) References Cited

U.S. PATENT DOCUMENTS

| | | | | | |
|---|---|---|---|---|---|
| 4,784,729 | A | * | 11/1988 | Jasinski | 205/775.5 |
| 4,840,719 | A | * | 6/1989 | Jasinski | 204/404 |
| 5,015,355 | A | * | 5/1991 | Schiessl | 204/404 |
| 5,139,627 | A | * | 8/1992 | Eden et al. | 205/775.5 |
| 5,306,414 | A | * | 4/1994 | Glass et al. | 204/404 |
| 5,519,330 | A | * | 5/1996 | Yamauchi et al. | 324/700 |
| 6,132,593 | A | * | 10/2000 | Tan | 205/776.5 |
| 6,540,902 | B1 | * | 4/2003 | Redey et al. | 205/354 |
| 6,683,463 | B2 | * | 1/2004 | Yang et al. | 324/700 |
| 6,987,396 | B2 | * | 1/2006 | Yang et al. | 324/700 |
| 7,309,414 | B2 | * | 12/2007 | Yang | 205/775.5 |
| 7,508,223 | B1 | * | 3/2009 | Yang et al. | 324/700 |
| 7,632,384 | B1 | * | 12/2009 | Redey et al. | 204/422 |
| 7,675,297 | B1 | * | 3/2010 | Yang et al. | 324/700 |
| 7,678,260 | B1 | * | 3/2010 | Yang et al. | 205/775.5 |
| 7,713,405 | B2 | * | 5/2010 | Jovancicevic et al. | 205/775.5 |
| 7,722,748 | B2 | * | 5/2010 | Chiang et al. | 204/404 |
| 7,982,474 | B1 | * | 7/2011 | Hefner et al. | 324/700 |
| 2003/0169058 | A1 | * | 9/2003 | Pierre et al. | 324/700 |
| 2007/0193887 | A1 | * | 8/2007 | Tormoen et al. | 205/775.5 |

OTHER PUBLICATIONS

U.S. Appl. No. 12/512,618, filed Jul. 30, 2009. Rathnamma, Dasara V. and Nagarajan, R. "Surface Chemical Studies of Hot Corrosion Life Prediction Model for Marine Gas Turbine Blades and Guide Vanes", pp. 1377-1383.
Rapp, Robert A. "Hot Corrosion of Materials: A Fluxing Mechanism?", *Corrosion Science* 44 (2002), pp. 209-221.

* cited by examiner

*Primary Examiner* — Carol Tsai
(74) *Attorney, Agent, or Firm* — Dority & Manning, P.A.

(57) ABSTRACT

A system and method for online monitoring of molten salt corrosion of a component of an apparatus is disclosed. First and second electrodes are electrically isolated from each other within the component and exposed to a corrosive operating environment of the apparatus. The first and second electrodes are electrically coupled such that when an electrical potential difference exists between the first and second electrodes an electrical current flows between the first electrode and the second electrode. The electrical potential difference between the first electrode and the second electrode is based at least in part on molten salt corrosion at the first electrode or the second electrode. At least one of the electrical potential difference or the electrical current flowing between the first electrode and second electrode is measured and analyzed such that a corrosion characteristic of the component can be predicted.

20 Claims, 2 Drawing Sheets

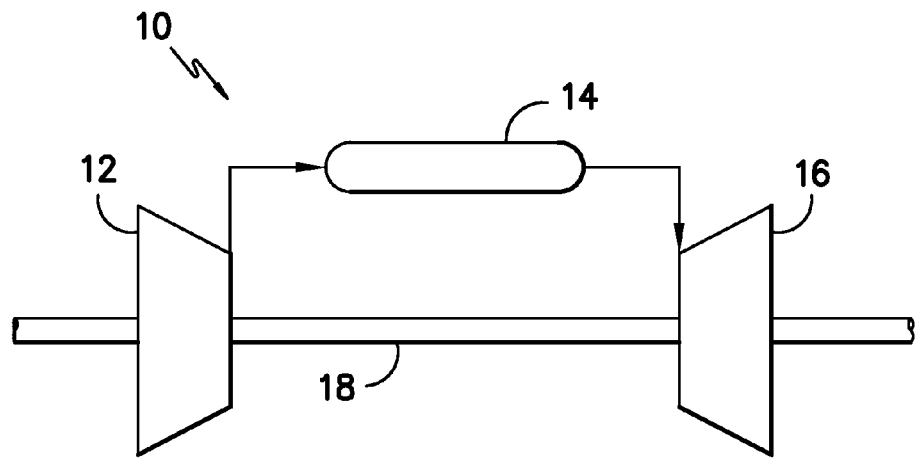
FIG. -1-
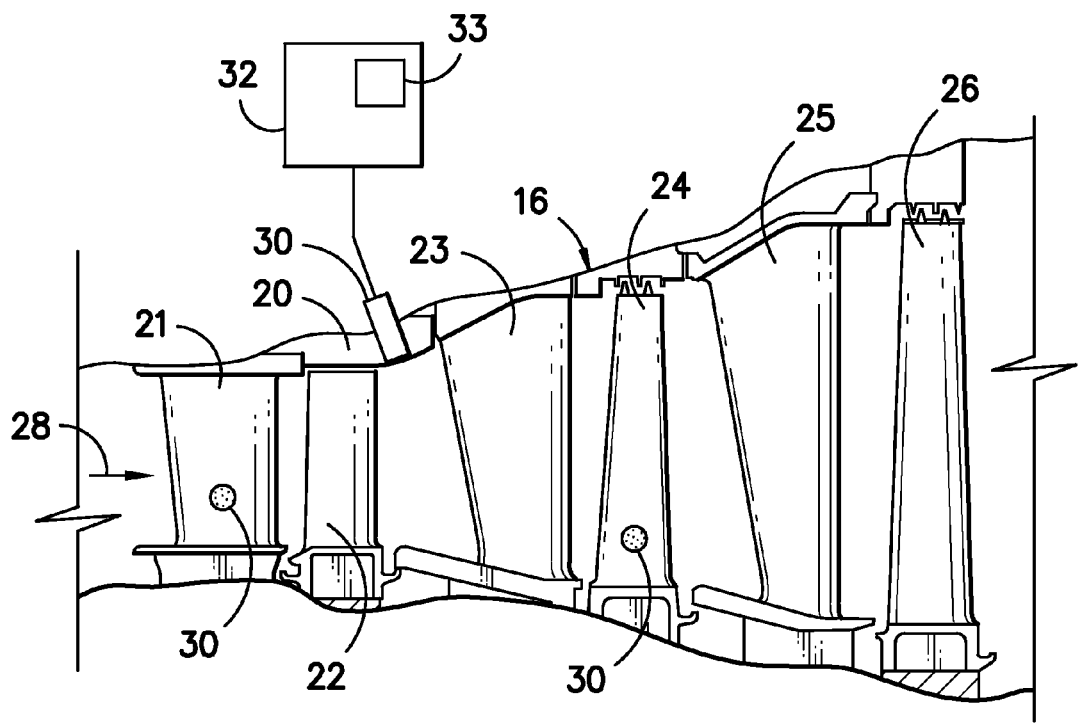
FIG. -2-

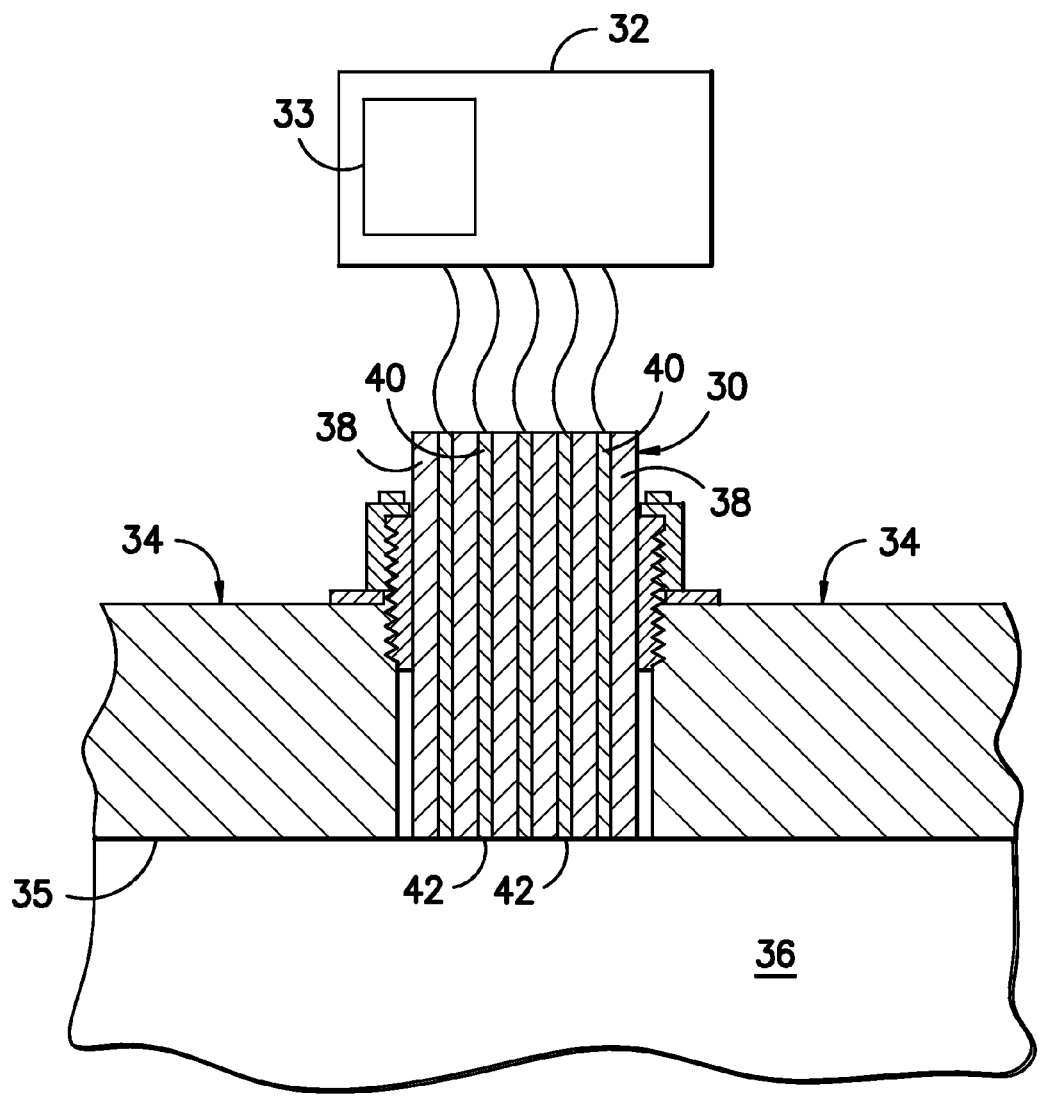
FIG. -3-

SYSTEM AND METHOD FOR ONLINE MONITORING OF MOLTEN SALT CORROSION

FIELD OF THE INVENTION

The present subject matter relates generally to corrosion monitoring and particularly to a system and method for online monitoring of molten salt corrosion of high temperature components.

BACKGROUND OF THE INVENTION

Electrochemical corrosion is a process in which a metal atom oxidizes and loses electrons. In corrosion parlance, the location at which metal atoms lose electrons is called the anode and the location where the electrons are transferred is called the cathode. Localized corrosion within a base metal involves the creation of actively corroding anode areas separated from the non-corroding cathode areas. Thus, as the base metal oxidizes at the anode, forming a pit in the anodic area, the electrons left behind flow to the cathode. Additionally, at the metal surface, ions in the liquid phase accept electrons released by the metal. This flow of electrons and ions forms essentially an electrical circuit. As such, when the circuit is closed and an electrical potential difference exists between the anode and the cathode, an electrical current flows between the anode and the cathode.

A particular type of corrosion, molten salt induced corrosion or hot corrosion, can be a major problem in many high temperature applications. For example, condensing molten salt environments can exist in turbine engines, aircraft engines, micro turbines, and various industrial chemical processes. In a gas turbine, specifically, fuel impurities, such as sulfites, vanadium, or chloride, flowing in the hot gas path can interact at high temperatures to form molten salts on the surfaces of many of the hot gas path components within a gas turbine. For example, a molten salt layer may form on the surfaces of the buckets or nozzles in the turbine section of a gas turbine. This molten salt layer can dissolve away the metal oxide surface layer of such components, exposing the base metal to oxygen from the gases flowing in the hot gas path and, thereby, cause rapid oxidation of the base metal.

Currently, one of the only means for monitoring most industrial equipment exposed to molten salt corrosion is shut down and inspection of the equipment. For gas turbines, in particular, downtime can be very costly. Additionally, inspections often necessitate dismantlement of at least a portion of the gas turbine, which requires further downtime and expense. Other options may be available to a gas turbine operator, such as fuel quality monitoring and filter maintenance, but it is difficult to predict when such actions need to be taken. As such, unnecessary expenditures are made when any of these actions are performed too frequently or too infrequently.

Accordingly, a system and method for online monitoring of molten salt corrosion of high temperature components would be welcome in the technology.

BRIEF DESCRIPTION OF THE INVENTION

Aspects and advantages of the invention will be set forth in part in the following description, or may be obvious from the description, or may be learned through practice of the invention.

In one aspect, the present subject matter provides a method for online monitoring of molten salt corrosion of a component of an apparatus. The method generally includes exposing a portion of a first electrode and a second electrode to a corrosive, operating environment of the apparatus. The first and second electrodes are disposed within the component and electrically isolated from each other by an insulating material. Additionally, the first and second electrodes are electrically coupled such that, when an electrical potential difference exists between the first and second electrodes, an electrical current flows between the first electrode and the second electrode. The method also includes measuring and analyzing at least one of the electrical potential difference or the electrical current flowing between the first electrode and second electrode in order to predict a corrosion characteristic of the component, wherein the electrical potential difference between the first electrode and the second electrode is based at least in part on molten salt corrosion at the first electrode or the second electrode.

In another aspect, the present subject matter provides a system for online monitoring of molten salt corrosion of a component of an apparatus. The system includes a corrosion sensing device disposed in the component of the apparatus. The corrosion sensing device generally includes a first electrode and a second electrode electrically isolated from each other within an insulating material. The first and second electrodes are arranged in the corrosion sensing device such that a portion of each of the first and second electrodes is exposed to a corrosive, operating environment within the apparatus. Additionally, the first and second electrodes are electrically coupled such that when an electrical potential difference exists between the first and second electrodes, an electrical current flows between the first electrode and the second electrode. The system of the present subject matter also includes a corrosion monitoring device configured to measure and analyze at least one of the electrical potential difference or the electrical current flowing between the first electrode and the second electrode such that a corrosion characteristic of the component can be predicted, wherein the electrical potential difference between the first electrode and the second electrode is based at least in part on molten salt corrosion at the first electrode or the second electrode.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWING

A full and enabling disclosure of the present invention, including the best mode thereof, directed to one of ordinary skill in the art, is set forth in the specification, which makes reference to the appended figures, in which:

FIG. 1 illustrates a schematic depiction of a gas turbine system;

FIG. 2 illustrates a sectional side view of a turbine section of a gas turbine with an embodiment of a system for the online monitoring of molten salt corrosion installed in accordance with an aspect of the present subject matter; and FIG. 3 illustrates a sectional side view of an embodiment of a corrosion sensing device coupled to a corrosion monitoring device in accordance with an aspect of the present subject matter.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally, the present subject matter discloses a system and method for online monitoring of molten salt corrosion. In particular, a system is disclosed that utilizes a corrosion sensing device and a corrosion monitoring device to detect and monitor molten salt corrosion of a high temperature component of an apparatus. For example, hot gas path components of a gas turbine may be subject to molten salt corrosion due to the formation of molten salts on their surfaces. As such, the present subject matter may provide operators of gas turbines with real-time information regarding corrosion rates of turbine components to permit proactive or reactive corrective actions to be performed on the gas turbine in order to prevent component damage.

It should be appreciated that the present subject matter will be generally described in reference to turbine components of a turbomachine, and particularly to components within the turbine section of an industrial gas turbine. However, it should be understood that the system and method of the present subject matter may be adapted for use with gas turbines used in propulsion applications, as well as various other applications in which molten salt corrosion may exist. Moreover, it should be readily appreciated that the present system and method may be generally utilized to provide online monitoring of molten salt corrosion of any high temperature component. For example, molten salt corrosion may occur in various high temperature applications in which a component of an apparatus is exposed to temperatures above the melting point of corrosive salts.

Generally, molten salt corrosion occurs when molten salts form on the surface of a metal component, dissolving away any metal oxide surface layer and exposing the base metal of the component to oxidants, such as oxygen. For example, molten salt corrosion may occur when a molten alkali salt forms on the surface of a turbine component, such as one formed from a nickel or cobalt-based superalloy. Current literature describes the corrosion mechanism of molten salt corrosion as one in which the dissolution of the oxide surface layer of a metal component permits oxygen and sulfite ions present in the molten salt to rapidly oxidize the metal. Specifically, it is currently understood by those of ordinary skill in the art that the oxidation occurring due to molten salt formation is localized at the interface between the molten salt and the metal atoms at the surface of a metal component. As such, it is believed that there is no significant electron transport through the metal component as a result of the corrosion.

Through experimentation, the inventors of the present subject matter have unexpectedly discovered that the oxidation associated with molten salt corrosion does, in fact, produce a detectable and measureable flow electrons as portions of the base metal oxidize in the presence of molten salts. Particularly, laboratory experiments have indicated that, when a molten salt is in contact with both a metal sensing electrode and a metal component or with two metal sensing electrodes, a current flow can be detected between the electrode and component (or between the two electrodes). Thus, the inventors of the present subject matter have found that the corrosion mechanism of molten salt corrosion is similar to that of many types of electrochemical corrosion. As such, when a metal component is exposed to oxidants due to the dissolution of its oxide surface layer in the presence of molten salts, the base metal is converted to a metal oxide, leaving behind electrons that, instead of being transported into the molten salt surface layer, may flow to other parts of the base metal (i.e. cathodic areas). This flow of electrons may then be measured to determine a corrosion characteristic of the base metal. As used herein, the term "corrosion characteristic" or "corrosion characteristics" generally refers to how a metal typically responds to corrosion, such as the pitting rates or the pitting depths due to corrosion. Generally, pits formed by corrosion continue to grow over time and can destroy the structural integrity of a metal component, which can lead to component failure.

Accordingly, to permit the detection of molten salt corrosion of a high temperature component, such as a hot gas path component, a corrosion sensing device may be installed in the component to sense the flow of electrons occurring as a result of the high temperature corrosion. Generally, the corrosion sensing device may be configured to simulate the base metal of the component, such as by simulating the anodic and cathodic areas of the base metal and by having corrosion characteristics similar to those of the component. Thus, in one embodiment, the corrosion sensing device may comprise a coupled multi-electrode array sensor, specifically adapted for use in a high temperature application, that utilizes an array of electrodes to simulate the anodic and cathodic regions of a corroding metal. The electrodes may be coupled together such that, when an electrical potential difference exists between the electrodes, an electrical current flows between the anode electrodes and the cathode electrodes. This electrical potential difference and/or electrical current may then be measured and analyzed by the corrosion monitoring device of the present subject matter to predict a corrosion characteristic, such as pitting rates and pitting depths, of the high temperature component and thereby determine when a corrective action is required to be performed on the component or the apparatus in which it is installed.

Accordingly, the system of the present subject matter may permit molten salt corrosion of a high temperature component to be continuously monitored so as to provide operators with real-time information on the status of the corroding component(s), without the need for frequent shutdowns for inspection. Thus, the system can provide the necessary input for determining when and what corrective actions are required to be performed such that the need for corrective actions can be more accurately predicted. For example, in one embodiment, a gas turbine operator may be provided with one or more recommended or required corrective actions based on the extent of corrosion occurring within the gas turbine.

Referring to the drawings, FIG. 1 illustrates a schematic diagram of a gas turbine 10. The gas turbine 10 generally includes a compressor section 12, a plurality of combustors within a combustor section 14, and a turbine section 16. The compressor section 12 and turbine section 16 may be coupled by a shaft 18. The shaft 18 may be a single shaft or a plurality of shaft segments coupled together to form the shaft 18. During operation of the gas turbine 10, the compressor section 12 supplies compressed air to the combustors of the combustor section 14. Air and fuel are mixed and burned within each combustor and hot gases of combustion flow in a hot gas path from the combustor section 14 to the turbine section 16, wherein energy is extracted from the combustion gases to produce work.

Referring to FIG. 2, the turbine section 16 of a gas turbine 10 may include any number of turbine stages. In one embodiment, the turbine section 16 may include three stages. The first stage of the turbine section 16 may include a plurality of circumferentially spaced nozzles 21 and buckets 22. For example, the first stage nozzles 21 may be circumferentially spaced one from the other and fixed about the axis of the rotor. Additionally, the first stage buckets 22 may be also be circumferentially spaced one from the other and coupled to the shaft 18 for rotation therewith. Similarly, the second stage of the turbine section 16 may include a plurality of circumferentially spaced nozzles 23 and buckets 24. A third stage of the turbine section 16 is also illustrated and may include a plurality of circumferentially spaced nozzles 25 and buckets 26. One of ordinary skill in the art should appreciate that the various stages of the turbine section 16 are generally disposed in the hot gas path 28 of combustion products flowing from the combustor section 14. Additionally, it should be appreciated that an annular shroud 20 may encircle the tips of the turbine buckets 22,24,26 to define the outer boundary of the hot gas path through each stage.

In accordance with an aspect of the present subject matter, FIG. 2 also illustrates an embodiment of a system for online monitoring of molten salt corrosion within a gas turbine 10. The system generally includes a corrosion sensing device 30 disposed within a hot gas path component 34 (FIG. 3) of the turbine section 16 of a gas turbine 10 and a corrosion monitoring device 32 coupled to the corrosion sensing device 30. The monitoring device 32 may be configured to measure and analyze outputs from the sensing device 30 to predict a corrosion characteristic of the component 34 in which the sensing device 30 is installed. Based on the predicted corrosion characteristic(s), the monitoring device 32 may then determine when a corrective action(s) is recommended or required to be performed on the gas turbine 10 in order to prevent component and/or turbine damage due to excessive corrosion.

As shown in FIG. 2, the corrosion sensing device 30 may be disposed at various locations along the hot gas path 28 of the gas turbine 10. For example, in one embodiment, the corrosion sensing device 30 may be installed in the turbine shroud 20 of the turbine section 16. As illustrated, the corrosion sensing device 30 may be coupled to the corrosion monitoring device 32 by a wire. Additionally, in alternative embodiments, the corrosion sensing device 30 may be installed in one of the nozzles 21,23,25 or buckets 22,24,26 of the various stages of the turbine section 16. In such embodiments, the corrosion sensing device 30 may be in communication with the corrosion monitoring device 32 through wires or through a wireless transmitter, such as a radio-frequency transmitter. Generally, however, it should be appreciated that the corrosion sensing device 30 may be installed in any high temperature component that may be susceptible to molten salt corrosion due to the formation of molten salts and thus application of the sensing device 30 need not be limited to components 34 of a gas turbine 10. It should also be appreciated that multiple corrosion sensing devices 30 may be disposed within the gas turbine 10, within a single turbine component or within any other high temperature component.

FIG. 3 illustrates a cross-sectional view of a corrosion sensing device 30 disposed generally in a hot gas path component 34 of a gas turbine 10. It should be appreciated, however, that, in alternative embodiments, the component 34 need not be a hot gas path component, but may generally comprise any high temperature component of any high temperature apparatus which is subject to molten salt corrosion. As shown, the corrosion sensing device 30 is installed or mounted within the component 34 such that one end of the sensing device 30 is exposed to a corrosive operating environment 36 within the gas turbine 10. For example, in one embodiment, the component 34 may comprise the turbine shroud 20 of the turbine section 16 such that one end of the corrosion sensing device 30 is exposed to the combustion products flowing in the hot gas path of the gas turbine 10 and the opposing end extends from an exterior side of the shroud 20. In an alternative embodiment, the component 34 may comprise a turbine bucket 22,24,26 or a turbine nozzle 21,23,25 such that one end of the sensing device 30 is exposed to the hot gases of combustion while the opposing end extends into the interior of the bucket 22,24,26 or the nozzle 21,23,25. Additionally, it should be appreciated that the corrosion sensing device 30 may be mounted within the component 34 using any suitable means. As shown, the sensing device 30 is secured in the component 34 by a swagelock-type compression fitting. In alternative embodiments, however, the corrosion sensing device 30 may be mounted within the component 34 utilizing a threaded fitting, by welding or by any other means known in the art.

Due to the discovery that the corrosion mechanism of molten salt corrosion results in the detectable flow of electrons, the corrosion sensing device 30 may generally comprise any mechanism or device capable of detecting the flow of electrons occurring due to high temperature corrosion. Thus, in one embodiment, the corrosion sensing device 30 of the present subject matter may comprise a coupled multi-electrode array sensor for detecting molten salt corrosion and may be configured as such. For example, the corrosion sensing device 30 may include an insulating material 38 and a plurality of electrodes 40. The insulating material 38 may generally be made of any material that resists the flow of electrical current so as to electrically isolate the electrodes 40 within the sensing device 30. In one embodiment, the insulating material 38 may comprise a material capable of withstanding the high temperatures within the turbine section 16 of the gas turbine 10. For example, the insulating material 38 may comprise a high temperature ceramic or some other suitable electrical insulator coated with a high temperature material.

The electrodes 40 of the corrosion sensing device 30 may comprise small pieces of metal or wire. Generally, the electrodes 40 may be disposed within the corrosion sensing device 30 such that each electrode 40 is electrically isolated from other electrodes 40 by the insulating material 38. Additionally, although a single row of electrodes 40 is illustrated in FIG. 3, it should be appreciated that the electrodes 40 may be arranged within the corrosion sensing device 30 as a two-dimensional array. Further, the spacing between adjacent electrodes 40 may generally vary. However, it should be appreciated that optimal spacing may be ascertainable through routine experimentation.

Moreover, the electrodes 40 may be arranged in the corrosion sensing device 30 such that a portion of each electrode 40 is exposed to a corrosive operating environment 36 within the gas turbine 10. For example, as shown in FIG. 3, an end face 42 of each of the electrodes may be exposed to the operating environment 36 of the gas turbine 10 and may be substantially aligned with an exposed surface 35 of the component 34. Thus, in one embodiment, the end faces 42 may be exposed to the combustion products flowing in the hot gas path 28 (FIG. 2) of the turbine section 16 and, in particular, may be exposed to any molten salts formed on the surface 35 of the component 34.

Generally, the corrosion sensing device 30 may be configured to detect corrosion occurring on a high temperature component. In particular, in one embodiment, the corrosion sensing device 30 may detect localized molten salt corrosion within the turbine section 16 of the gas turbine 10 based on the electrochemical reactions occurring at the exposed faces 42 of the electrodes 40. For example, due to arrangement of the sensing device 30 in the component 34, the electrodes 40 may be exposed to the molten salts forming on the component surface 35 and, thus, undergo corrosion similar to that of the component 34. Some of the electrodes 40 within the corrosion sensing device 30 will have properties like the anodic sites in the base metal of the turbine component 34 and some of the electrodes will have properties like the cathodic sites of the base metal. Thus, when the electrodes 40 are electrically isolated from each other within the insulating material 38 but electrically coupled together external to the insulating material 38, such as within the corrosion monitoring device 32, the electrodes 40 operable as anodes may simulate the anodic areas and electrodes 40 operable as cathodes may simulate the cathodic areas of the base metal. As such, when an electrical potential difference exists between the electrodes, due to molten salt corrosion occurring at one or more of the anode electrodes 40, an electrical current may flow between the electrodes 40. Accordingly, the electrodes 40 operable as anodes may release electrons that flow to the electrodes 40 operable as cathodes. The resulting electrical potential difference and/or electrical current between the anode electrodes 40 and the cathode electrodes 40 may then be measured and analyzed by the corrosion monitoring device 32 to predict the extent of corrosion occurring on the component 34 and thereby determine when a corrective action, if any, may be required to be performed on the component 34, the gas turbine 10, or any other apparatus in which the corrosion sensing device 30 is installed.

Still referring to FIG. 3, it should be appreciated that the electrodes 40 may be formed from a material having corrosion characteristics similar to those of the material used to form the component 34. In one embodiment, the electrodes 40 may be formed from a material having corrosion characteristics substantially similar to those of the component 34. As such, the electrodes 40 may exhibit a corrosion behavior substantially similar to that of the component 34 and, more particularly, exhibit a similar response to the corrosive molten salts responsible for much of the corrosion within the turbine section 16 of a gas turbine 10. For example, in one embodiment, the electrodes 40 may be formed from the same material as the component 34, such as the same material as the turbine buckets 22,24,26, the turbine nozzles 21,23,25, or the turbine shroud 20 of the turbine section 16. Thus, the measurements taken from the corrosion sensing device 30 may not only indicate the corrosion characteristics of the electrodes 40, but, by appropriately choosing the electrode material, may also be used to accurately predict the extent of corrosion occurring at the surface 35 of the component 34. It should be appreciated that, in some embodiments, the electrodes 40 may be formed from a material that is more sensitive to corrosive agents, such as molten salts, than the material used to form the component 34 in order to increase the signal output of the corrosion sensing device 30.

Additionally, in further embodiments, the actual electrodes 40 may be formed from substantially different materials to permit the taking of corrosion measurements for multiple turbine components 34 using a single corrosion sensing device 30 and/or to allow additional information to be gathered relating to the corrosion occurring within the gas turbine 10 or on the component 34. For example, in one embodiment, a first set of electrodes 40 of the corrosion sensing device 30 may be formed from the same material as a particular turbine component 34, while a second set may be formed from the same material as a different component. As such, the electrical potential differences across and/or the electrical currents flowing between the first and second sets of electrodes 40 may be measured in order to predict the extent of corrosion occurring on both components 34 without necessitating the use of more than one sensing device 30. In another embodiment, the electrodes 40 of the corrosion sensing device 30 may each be formed from a different metal, with each metal exhibiting differing corrosion characteristics depending on the particular molten salt or combination of molten salts causing the corrosion. In such an embodiment, the electrical potential differences across and/or the electrical currents flowing between the electrodes 40 of differing materials may be measured and a particular transfer function developed in order to accurately predict which molten salt(s) may be causing the localized corrosion on the component 34. In an alternative embodiment, two or more sensing devices 30 may be disposed within an apparatus, such as a gas turbine 10, with at least one sensing device 30 including electrodes 40 formed from a material substantially similar to that of the component 34 in which it is installed and at least one other sensing device 30 including electrodes 40 made of differing materials.

As indicated above, the corrosion monitoring device 32 of the present subject matter may be generally configured to measure and analyze the outputs from the corrosion sensing device 30 (e.g. the electrical potential differences across and/ or the electrical currents flowing between the electrodes 40). Thus, in one embodiment, the corrosion monitoring device 32 may be utilized to predict the corrosion characteristics of a turbine component 34 and thereby indicate to a turbine operator when a corrective action may be recommended or required to be performed. In doing so, it should be appreciated that, in various embodiments, the electrodes 40 of the corrosion sensing device 30 may be electrically coupled within the corrosion monitoring device 32 such that the monitoring device 32 is capable of measuring the electrical potential difference and/or the electrical current flowing between any two electrodes 40 or the electrical potential difference and/or the electrical current flowing between a plurality of electrodes 40 disposed within the corrosion sensing device 30.

Generally, the corrosion monitoring device 32 may comprise any device or combination of devices capable of measuring and analyzing the potential difference across and/or the electrical current flowing between the electrodes 40. For example, the corrosion monitoring device 32 may comprise a voltmeter, ammeter or any other suitable electrical measuring instrument in communication with the turbine controller of a turbine control system, some other computer or any other suitable processing equipment. Thus, in one embodiment, each of the electrodes 40 may be electrically connected to a common lead (not illustrated), with a small resistor (not illustrated) connected between each electrode and the common lead. The output from each electrode 40 may be delivered to a multi-channel voltmeter such that the electrical potential difference or voltage drop across the resistor may be measured. Voltage measurements may then be transmitted to any suitable processing equipment, such as a computer, to analyze the measurements. In an alternative embodiment, the corrosion monitoring device 32 may include a multi-electrode corrosion monitor in communication with suitable processing equipment such that the potential difference and/or electrical current between the electrodes 40 may be measured and analyzed. A suitable commercially available multi-electrode corrosion monitor may comprise a NANOCORR from CORR INSTRUMENTS (San Antonio, Tex.). In a further embodiment, the corrosion sensing device 30 may be directly coupled to processing equipment that is capable of both measuring and analyzing outputs from the sensing device 30 in order to predict the corrosion characteristics of the component 34. It should be appreciated that any processing equipment utilized with the system of the present subject matter, such as any computer-related equipment, may be configured to run any suitable set of software instructions for analyzing the potential differences and/or the electrical current between the electrodes 40.

As indicated above, the corrosion sensing device 30 may be generally configured to simulate the corroding base metal of a high temperature component, such as a hot gas path component 34 of a gas turbine 10. Thus, the corrosion monitoring device 32 can be employed to predict a corrosion characteristic of the component 34, such as pitting rates and depths, by analyzing the current flow between and/or the electrical potential difference across the electrodes 40. It should be appreciated that a suitable transfer function may be developed to relate the electrical potential difference, the electrical current flowing between the electrodes 40 or both to the corrosion characteristics of the component 34. The development of such transfer functions is within the capability of those skilled in the art, and therefore will not be discussed in any detail herein. However, generally, average corrosion or pitting rates of the component 34 may be predicted based on the average of the currents between the anodic and cathodic electrodes 40 and localized corrosion rates may be predicted based on the fastest corroding electrode 40 (i.e. the most anodic electrode from which electrons are lost at the highest rate). Additionally, corrosion or pitting depth may be predicted by reverse-calculating base metal loss at the anodic electrodes 40 via measuring current.

The corrosion monitoring device 32 may also be capable of manipulating, storing and/or displaying the predicted corrosion characteristics and/or corrosion measurements so that such data may be accessed and understood by an operator or maintenance worker. For example, the corrosion monitoring device 32 may include a display device 33, such as a computer screen, display panel or other suitable visual display, which provides the operator with a visual indication of the extent of corrosion occurring on the component 34. Thus, in one embodiment, the corrosion monitoring device 32 may be configured to display on the display device 33 a table or chart depicting the predicted pitting depth and/or pitting rate over time for a particular turbine component 34, multiple turbine components or for the gas turbine 10, in general. In such an embodiment, the gas turbine operator may then determine what corrective action, if any, is necessary to respond to the displayed pitting rates and/or pitting depths. Alternatively, the corrosion monitoring device 32 may be programmed with suitable software instructions so as to automatically determine whether a corrective action is necessary based on, for example, predetermined limits for pitting depths and/or pitting rates for the particular component(s) 34. As such, the corrosion monitoring device 32 may notify a gas turbine operator or maintenance worker, via the display device 33, automatically of any recommended or required corrective actions to permit the operator to take any necessary actions.

Thus, by associating the electrical potential difference measurements and/or the electrical current measurements with the corrosion characteristics of the component 34, the corrosion monitoring device 32 may also be utilized to indicate when a corrective action should be preformed on the gas turbine 10 or the component 34, itself. This may allow for both predictive/proactive maintenance of a gas turbine 10, as well as the performance of reactive corrective actions based on, for example, a sudden or unexpected increase in corrosion levels. The corrective action taken may generally be any action directed towards preventing or reducing the amount of molten salt corrosion occurring on the component 34 or any action directed to monitoring and/or inspecting the status of component 34. For example, the corrective action may comprise shutting down and inspecting portions of the gas turbine 10 or altering machine operating parameters, such as reducing or increasing firing temperature, switching fuel types, adding a fuel corrosion inhibitor and/or adjusting turndown of the machine. It should be appreciated that various other corrective actions may be apparent to those of ordinary skill in the art and, thus, the potential corrective actions need not be limited to the actions discussed above.

Additionally, it should be appreciated that the particular corrective action taken may depend on the type and/or extent of corrosion predicted for a particular turbine component 34. For example, it may be desirable to relate and/or assign certain corrective actions or a combination of corrective actions to a particular corrosion condition/rate/status to enable a gas turbine operator (or the corrosion monitoring device 32) to quickly determine what action should be taken. Thus, in one embodiment, if the predicted pitting rate for a component 34 exceeds a predetermined pitting rate, the corrective action may comprise the implementation of any available mitigation strategies, such as altering certain machine operating parameters. Similarly, if the predicted pitting depth for a component 34 exceeds a predetermined pitting depth, the machine may be shut down and inspected to prevent component failure. Further, if analysis of the measurements taken from the corrosion sensing device 30 indicates that the predicted pitting rate for a component 34 has significantly increased over a short period of time, special causes for such an increase (e.g. fuel quality changes or filter equipment malfunction) may be investigated by the operator.

Moreover, it should be appreciated that, by combining the measurements from the corrosion monitoring device 32 with other available data (e.g. turbine operating hours, component operating hours, operating temperatures, etc), the operating life of a turbine component 34 may also be predicted. For example, it should be appreciated that a suitable transfer function may be developed to accurately predict component life based, at least in part, on the corrosion measurements provided by the corrosion monitoring device 32.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for online monitoring of molten salt corrosion of a high temperature component of an apparatus, the method comprising:

exposing a portion of a first electrode and a second electrode to a corrosive operating environment of an apparatus, wherein said first electrode and said second electrode are disposed within a component of the apparatus and electrically isolated from each other by an insulating material, said first and second electrodes being electrically coupled such that when an electrical potential difference exists between said first electrode and said second electrode an electrical current flows between said first electrode and said second electrode;

measuring at least one of the electrical potential difference or the electrical current flowing between said first electrode and said second electrode; and analyzing the at least one of the measured electrical potential difference or the measured electrical current to predict a corrosion characteristic of said component, wherein the electrical potential difference between said first electrode and said second electrode is based at least in part on molten salt corrosion at said first electrode or said second electrode.

2. The method of claim 1, comprising determining when to perform a corrective action on the apparatus based on the predicted corrosion characteristic of said component.

3. The method of claim 1, comprising performing a corrective action on the apparatus based on the predicted corrosion characteristic of said component.

4. The method of claim 3, wherein the apparatus comprises a gas turbine and said corrective action comprises shutting down and inspecting the gas turbine.

5. The method of claim 3, wherein the apparatus comprises a gas turbine and said corrective action comprises adjusting one or more machine operating parameters of the gas turbine.

6. The method of claim 1, comprising visually displaying the predicted corrosion characteristic of said component.

7. The method of claim 1, wherein the corrosion characteristics of said component comprises at least one of pitting depth or pitting rate.

8. The method of claim 1, wherein said first and second electrodes are formed from a material having a corrosion characteristic substantially similar to that of said component.

9. The method of claim 1, wherein said first and second electrodes form part of a corrosion sensing device, said corrosion sensing device including a plurality of electrodes.

10. The method of claim 1, wherein the apparatus comprises a gas turbine.

11. The method of claim 10, wherein said component comprises a hot gas path component of the gas turbine.

12. A method for online monitoring of molten salt corrosion of a component of a gas turbine, the method comprising:

exposing a portion of a first electrode and a second electrode to a corrosive operating environment of a gas turbine, wherein said first electrode and said second electrode are disposed within a component of the gas turbine and electrically isolated from each other by an insulating material, said first and second electrodes being formed from a material having a corrosion characteristic substantially similar to that of said component, said first and second electrodes being electrically coupled such that when an electrical potential difference exists between said first electrode and said second electrode an electrical current flows between said first electrode and said second electrode;

measuring at least one of the electrical potential difference or the electrical current flowing between said first electrode and said second electrode; and analyzing the at least one of the measured electrical potential difference or the measured electrical current to predict the corrosion characteristic of said component; and determining when to perform a corrective action on the gas turbine based on the predicted corrosion characteristic of said component, wherein the electrical potential difference between said first electrode and said second electrode is based at least in part on molten salt corrosion at said first electrode or said second electrode.

13. The method of claim 12, comprising performing the corrective action on the gas turbine, wherein the corrective action comprises shutting down and inspecting the gas turbine or adjusting one or more machine operating parameters of the gas turbine.

14. A system for online monitoring of molten salt corrosion of a component of an apparatus, the system comprising:

a corrosion sensing device disposed in a component of an apparatus, said corrosion sensing device comprising a first electrode and a second electrode electrically isolated from each other within an insulating material, said first and second electrodes being arranged such that a portion of each of said first and second electrodes is exposed to a corrosive operating environment within the apparatus, said first and second electrodes being electrically coupled such that when an electrical potential difference exists between said first electrode and said second electrode an electrical current flows between said first electrode and said second electrode, the electrical potential difference between said first electrode and said second electrode being based at least in part on molten salt corrosion at said first electrode or said second electrode; and a corrosion monitoring device configured to measure and analyze at least one of the electrical potential difference or the electrical current flowing between said first electrode and said second electrode such that a corrosion characteristic of said component can be predicted.

15. The system of claim 14, wherein the apparatus comprises a gas turbine and said component comprises a hot gas path component of the gas turbine.

16. The system of claim 14, wherein said component and said first and second electrodes are formed from the same material.

17. The system of claim 14, wherein said first and second electrodes are formed from a material more sensitive to corrosion than said component.

18. The system of claim 14, wherein said corrosion sensing device comprises a coupled multi-electrode array sensor, said first and second electrodes forming part of a plurality of electrodes isolated from each other within said insulating material.

19. The system of claim 18, wherein said corrosion sensing device includes a first set of electrodes and a second set of electrodes, said first set of electrodes being formed from a different material than said second set of electrodes.

20. The system of claim 14, wherein the corrosion characteristic of said component comprises at least one of pitting depth and pitting rate.

* * * * *